United States Patent [19]

Buchel et al.

[11] 4,073,901
[45] Feb. 14, 1978

[54] METAL COMPLEXES OF N-TRITYL-AZOLES FOR COMBATTING FUNGI

[75] Inventors: Karl Heinz Buchel, Wuppertal; Paul-Ernst Frohberger; Helmut Kaspers, both of Leverkusen, all of Germany

[73] Assignee: Bayer Aktiengesellschaft, Leverkusen, Germany

[21] Appl. No.: 649,161

[22] Filed: Jan. 14, 1976

[30] Foreign Application Priority Data

Jan. 24, 1975 Germany .......................... 2502932

[51] Int. Cl.² ...................... A61K 31/555; C07F 1/08; C07F 3/06
[52] U.S. Cl. ...................... 424/245; 260/299; 260/308 R; 548/345; 424/269; 424/273 R
[58] Field of Search ............... 260/299, 308 R, 309; 424/245, 269, 273

[56] References Cited

U.S. PATENT DOCUMENTS

| | | | |
|---|---|---|---|
| 3,321,366 | 5/1967 | Mussell et al. | 424/273 |
| 3,647,810 | 3/1972 | Bayer et al. | 260/299 |
| 3,682,950 | 8/1972 | Buchel et al. | 260/308 R |
| 4,005,083 | 1/1977 | Buchel et al. | 424/245 |

FOREIGN PATENT DOCUMENTS

| | | |
|---|---|---|
| 1,670,976 | 6/1971 | Germany. |
| 2,213,863 | 10/1973 | Germany. |
| 1,670,977 | 2/1971 | Germany. |

Primary Examiner—R. J. Gallagher
Assistant Examiner—Diana G. Rivers
Attorney, Agent, or Firm—Burgess, Dinklage & Sprung

[57] ABSTRACT

Metal complexes of N-trityl-azoles of the formula (I)

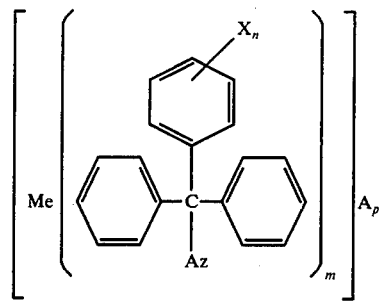

in which
  Me is a metal,
  X is halogen, nitro, cyano, hydroxyl, alkyl, alkoxy, alkylthio, alkoxycarbonyl, haloalkyl or alkylsulfonyl,
  Az is an imidazolyl radical or a 1,2,4-triazolyl radical,
  A is an anion of an inorganic acid,
  $n$ is 0, 1, 2, 3 or 4,
  $m$ is 1, 2, 3 or 4, and
  $p$ is 1, 2, 3, 4, 5 or 6, which possess fungicidal properties.

10 Claims, No Drawings

METAL COMPLEXES OF N-TRITYL-AZOLES FOR COMBATTING FUNGI

The present invention relates to and has for its objects the provision of particular new metal complexes of N-trityl-azoles, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples. The present invention relates to certain new metal complexes of N-trityl-azoles, to a process for their preparation and to their use as fungicides.

It has been disclosed in U.S. Pat. No. 3,321,366 and German Published Specification DOS 1,670,976 that N-tritylimidazoles, such as N-triphenylmethyl-imidazole (Compound A) and 1-(2-chlorophenyl-diphenylmethyl)-imidazole (Compound B), possess a good fungicidal activity. Furthermore it is known from German Published Specification DOS 1,670,977 that N-tritylimidazolium salts are fungicidally active. In addition, it has been disclosed in German Published Specification DOS 1,795,249 that 1-trityl-1,2,4-triazoles, such as 1-triphenylmethyl-1,2,4-triazole (Compound C), exhibit a good fungicidal action. However, the action of all these compounds is not always entirely satisfactory, expecially if low amounts are used. Furthermore, their toleration by plants is not always entirely satisfactory if high concentrations are used.

The present invention provides metal complexes of N-trityl-azoles of the formula

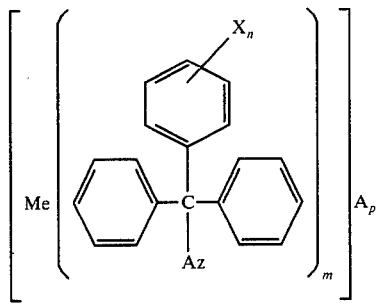
(I)

in which
Me is a metal,
X is halogen, nitro, cyano, hydroxyl, alkyl, alkoxy, alkylthio, alkoxycarbonyl, haloalkyl or alkylsulfonyl,
Az is an imidazolyl radical or a 1,2,4-triazolyl radical,
A is an anion of an inorganic acid,
$n$ is 0, 1, 2, 3 or 4,
$m$ is 1, 2, 3 or 4, and
$p$ is 1, 2, 3, 4, 5 or 6.

X preferably represents halogen, nitro, cyano, hydroxyl, straight-chain or branched alkyl with up to 6 carbon atoms, haloalkyl with 1 or 2 carbon atoms and up to 5 halogen atoms, especially fluorine or chlorine atoms, alkoxycarbonyl with a total of up to 5 carbon atoms, alkoxy with 1 or 2 carbon atoms, alkylthio with 1 or 2 carbon atoms, or alkylsulfonyl with 1 or 2 carbon atoms; $n$ preferably represents 0, 1, 2 or 3; Me preferably represents a metal of main groups II to IV and of sub-groups I, II and IV to VIII of the Periodic Table, especially copper, zinc, manganese, magnesium, tin, iron and nickel; A preferably represents a chloride, bromide, iodide, nitrate, sulfate or phosphate anion; and $p$ preferably represents 1, 2, 3 or 4.

Surprisingly, the metal complexes of N-trityl-azoles, according to the invention, exhibit a substantially greater fungicidal activity, especially against species of powdery mildew, than the known 1-trityl-imidazoles and -1,2,4-triazoles which are the most closely related known active compounds. The active compounds according to the invention thus represent an enrichment of the art.

The invention also provides a process for the production of a metal complex of the formula (I) in which a N-trityl-azole of the formula

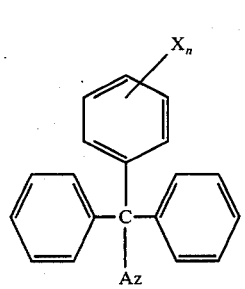
(II)

in which
X, Az and $n$ have the abovementioned meanings, is reacted with a metal salt of the formula

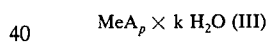

$$\text{MeA}_p \times k\ H_2O \quad (III)$$

in which
$k$ is a number from 0 to 12, and
Me, A and $p$ have the abovementioned meanings, in the presence of a solvent.

If 1-(m-chlorophenyl-diphenyl-methyl)-imidazole and copper-II chloride are used as starting materials, the course of the reaction can be represented by the following equation:

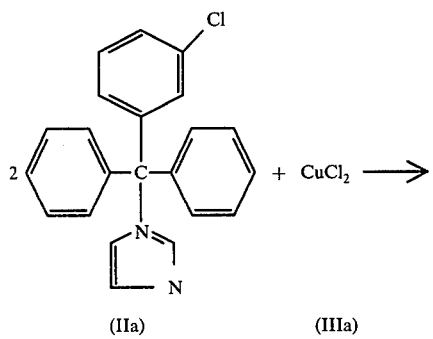
(1)

(IIa)      (IIIa)

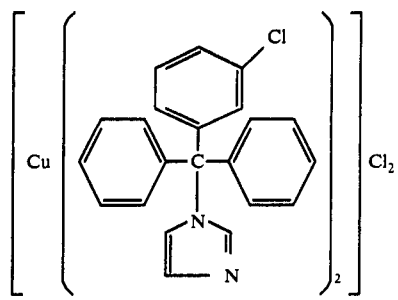

The starting materials of the formula (II) are generally known (German Published Specification DOS 1,670,976 or the corresponding British Patent Specification 1,260,588, U.S. Pat. No. 3,321,366, German Published Specification DOS 1,795,249 or the corresponding British Patent Specification 1,237,509 and German Published Specification DOS 2,213,863 or the corresponding South African Patent Specification 73-1981). Individual starting materials of the formula (II) which are not yet known can be obtained in accordance with known processes by, for example, reacting the corresponding trityl halides in the presence of an acid-binding agent and optionally in the presence of a diluent, or reacting the corresponding trityl-carbinols in the presence of a diluent with 1,2,4-triazoles or imidazoles.

The following compounds of the general formula

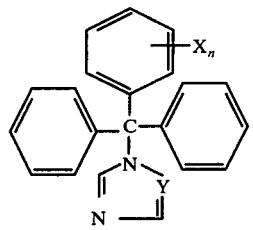

(IV)

may be mentioned individually as examples of the N-tritylazoles to be used, according to the invention, as starting materials:

| X | n | Y | X | n | Y |
|---|---|---|---|---|---|
| 2-F | 1 | CH | 3-CN | 1 | CH |
| 3-F | 1 | CH | 4-CN | 1 | CH |
| 4-F | 1 | CH | 2-CH$_3$ | 1 | CH |
| 2-Cl | 1 | CH | 3-CH$_3$ | 1 | CH |
| 3-Cl | 1 | CH | 4-CH$_3$ | 1 | CH |
| 4-Cl | 1 | CH | 2-C$_2$H$_5$ | 1 | CH |
| 2-Br | 1 | CH | 2-C$_3$H$_7$ | 1 | CH |
| 3-Br | 1 | CH | 4-n-C$_4$H$_9$ | 1 | CH |
| 4-Br | 1 | CH | 4-i-C$_4$H$_9$ | 1 | CH |
| 2-I | 1 | CH | 2-CF$_3$ | 1 | CH |
| 3-I | 1 | CH | 3-CF$_3$ | 1 | CH |
| 4-I | 1 | CH | 4-CF$_3$ | 1 | CH |
| 2-CN | 1 | CH | 2-OCH$_3$ | 1 | CH |
| 4-OCH$_3$ | 1 | CH | 2,6-OCH$_3$ | 2 | CH |
| 3-CO—OCH$_3$ | 1 | CH | 2-Cl | 1 | N |
| 4-CO—OCH$_3$ | 1 | CH | 3-Cl | 1 | N |
| 4-SCH$_3$ | 1 | CH | 4-Cl | 1 | N |
| 3-NO$_2$ | 1 | CH | 2-Br | 1 | N |
| 4-NO$_2$ | 1 | CH | 3-Br | 1 | N |
| 4-O$_2$S—CH$_3$ | 1 | CH | 2-F | 1 | N |
| 2-OH | 1 | CH | 4-F | 1 | N |
| 3-OH | 1 | CH | 2-CF$_3$ | 1 | N |
| 4-OH | 1 | CH | 3-CF$_3$ | 1 | N |
| 2,4-Cl | 2 | CH | 4-CF$_3$ | 1 | N |
| 2,3-Cl | 2 | CH | 2-CH$_3$ | 1 | N |
| 3,4-Cl | 2 | CH | 3-CH$_3$ | 1 | N |
| 2,5-Cl | 2 | CH | 2-CN | 1 | N |
| 3,5-Cl | 2 | CH | 3-CN | 1 | N |
| 2,6-Cl | 2 | CH | 4-CN | 1 | N |
| 2-CH$_3$, 4-Cl | 2 | CH | 3-NO$_2$ | 1 | N |
| 2-Cl, 4-SC$_2$H$_5$ | 2 | CH | 3-CO—OCH$_3$ | 1 | N |
| 3-NO$_2$, 4-Cl | 2 | CH | 4-CO—OCH$_3$ | 1 | N |
| 2,4-CH$_3$ | 2 | CH | 2,4-Cl | 2 | N |
| 3,5-CH$_3$ | 2 | CH | 3,4-Cl | 2 | N |
| 2,3-CH$_3$ | 2 | CH | 2,5-Cl | 2 | N |
| 2,5-CH$_3$ | 2 | CH | 2-CH$_3$, 4-Cl | 2 | N |

In formula (III) which covers the metal salts used for the preparation of the metal complexes according to the invention, $k$ preferably represents a number from 0 to 8.

The requisite metal salts of the formula (III) are generally compounds which have been known for a long time and are easily prepared.

Possible diluents for the reaction according to the invention include water and all inert organic solvents. Preferred ones include alcohols, such as methanol and ethanol, ketones, such as acetone, and ethers, such as diethyl ether and dioxane.

The reaction temperatures can be varied within a substantial range. In general, the reaction is carried out at 0° to 40° C, preferably at 15° to 25° C.

In carrying out the process according to the invention, the stoichiometric amount (depending on the oxidation level of the metal) of the compound of the formula (II) is generally employed per mole of the metal salt (III). Exceeding these ratios by up to 20 mole % is possible without significant reduction in yield. The mixture may be worked up in a manner which is customary for organic compounds and is generally known, for example by filtering off the complex which has precipitated and purifying it by recrystallization, for example from alcohol.

The active compounds according to the invention exhibit a powerful fungitoxic action. They do not harm crop plants in the concentrations required for combating fungi. For these reasons, they are suitable for use as plant protection agents for combating fungi. Fungitoxic agents are employed in plant protection to combat *Archimycetes, Phycomycetes, Ascomycetes, Basidiomycetes* and *Fungi Imperfecti.*

The active compounds according to the invention have a very broad spectrum of action and can be used against parasitic fungi which infest above-ground parts of plants or attack the plants through the soil, and against pathogens which can be transferred by seeds.

They display a particularly good action against parasitic fungi on above-ground parts of plants, such as species of *Erysiphe,* species of *Podosphaera* and species of *Venturia* and also against species of *Piricularia* and species of *Pellicularia.* It is to be emphasized that the active compounds according to the invention not only possess a protective action but are also curatively active, that is to say they can be employed after the infection has occurred. As plant protection agents, the compounds according to the invention can be used for the treatement of seed and soil as well as for the treatment of above-ground parts of plants.

The compounds according to the invention are well tolerated by plants. They have only a low toxicity to warm-blooded animals and because of their low odor and their good toleration by human skin, they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, bactericides, rodenticides, herbicides, fertilizers, growth-regulating agents, plant nutrients, agents for improving soil structure, bird repellents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.00001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, the active compound concentrations in the application forms can be varied within a substantial range. They are in general from 0.1 to 0.00001 percent by weight, preferably 0.05 to 0.001%.

In the treatment of seed, amounts of active compound of 0.001 to 50 g per kilogram of seed, preferably 0.01 to 10 g, are in general required.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown, to a domestic animal or to stored seed, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of coure, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Shoot treatment test/powdery mildew of cereal/protective (leaf-destructive mycosis)

To produce a suitable preparation of active compound, 0.25 g part by weight of active compound was taken up in 25 parts by weight of dimethylformamide and 0.06 part by weight of alkylaryl polyglycol ether emulsifier and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of *Erysiphe graminis* var. hordei.

After 6 days dwell time of the plants at a temperature of 21–22° C and 80–90% atmospheric humidity the occurrence of mildew pustules on the plants was evaluated. The degree of infection is expressed as a percentage of the infection of the untreated control plants. 0% denotes no infection and 100% denotes the same degree of infection as in the case of the untreated control. The active compound is the more active, the lower is the degree of mildew infection.

The active compounds, active compound concentrations in the spray liquor and degrees of infection can be seen from the table which follows:

Table 1

| Active compound | | Active compound concentration in the spray liquor in % by weight | Infection in % of the untreated control |
|---|---|---|---|
| untreated | | — | 100 |
| 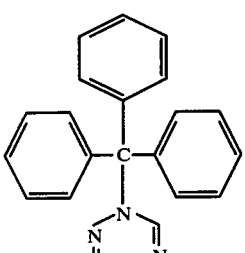 (known) | (C) | 0.01<br>0.0025<br>0.001 | 50.0<br>68.8<br>68.8 |
| 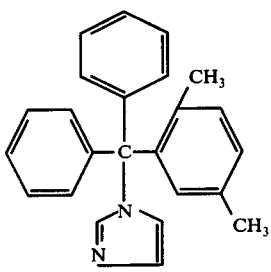 (known) | (D) | 0.03<br>0.01 | 50.0<br>77.5 |
| 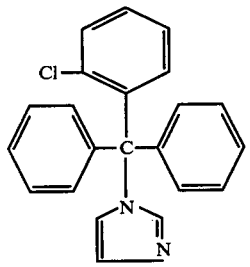 (known) | (B) | 0.01<br>0.003<br>0.001 | 25.0<br>35.0<br>85.0 |
| 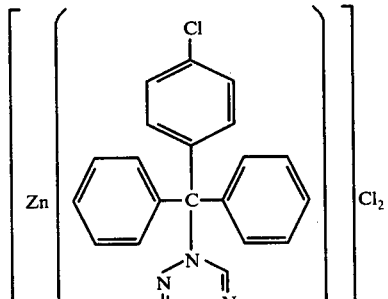 | (17) | 0.01<br>0.0025<br>0.001 | 0.0<br>0.0<br>31.9 |

Table 1-continued
Shoot treatment test/powdery mildew of cereal/protective
| Active compound | | Active compound concentration in the spray liquor in % by weight | Infection in % of the untreated control |
|---|---|---|---|
| 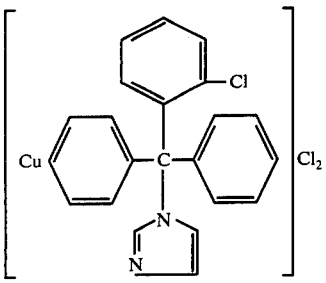 | (3) | 0.0025<br>0.001 | 14.4<br>30.0 |
| 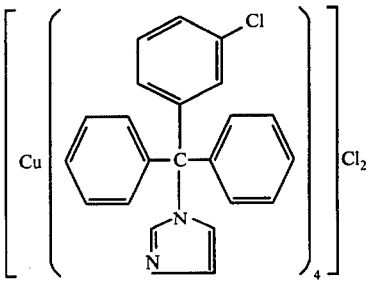 | (4) | 0.01<br>0.0025 | 0.0<br>12.5 |
| 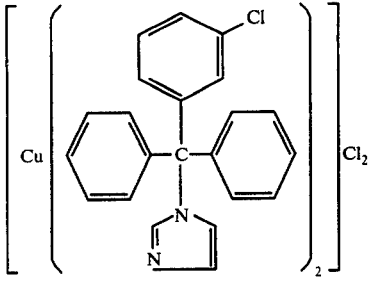 | (1) | 0.025<br>0.01<br>0.005<br>0.0025 | 0.0<br>0.0<br>12.5<br>31.3 |
| 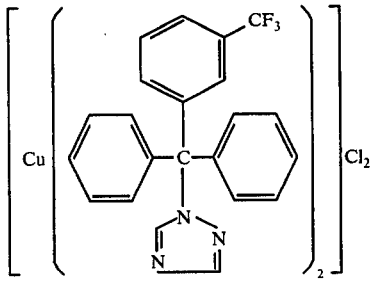 | (5) | 0.01<br>0.0025 | 0.0<br>21.3 |
| 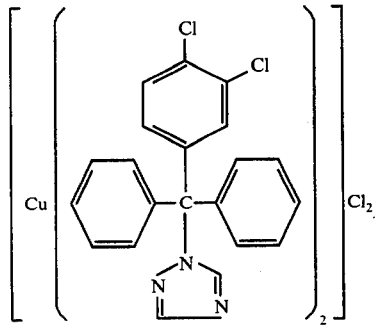 | (7) | 0.01<br>0.0025 | 0.0<br>33.8 |

Table 1-continued
Shoot treatment test/powdery mildew of cereal/protective
| Active compound | | Active compound concentration in the spray liquor in % by weight | Infection in % of the untreated control |
|---|---|---|---|
| 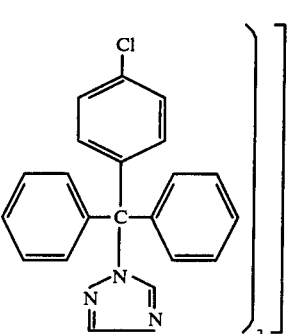 | (8) | 0.01<br>0.0025 | 5.0<br>33.8 |
| 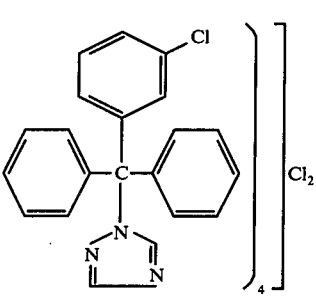 | (9) | 0.01<br>0.0025<br>0.001 | 0.0<br>0.0<br>21.3 |
| 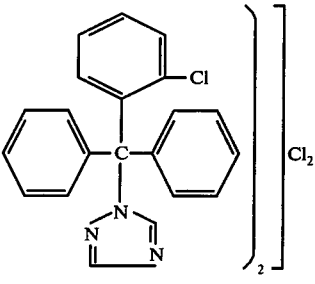 | (10) | 0.01<br>0.0025<br>0.001 | 0.0<br>0.0<br>25.0 |
| 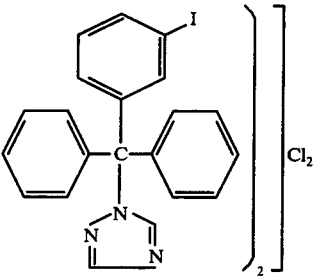 | (11) | 0.01<br>0.0025 | 0.0<br>16.3 |
| 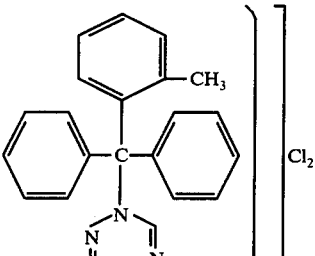 | (12) | 0.01<br>0.0025<br>0.001 | 0.0<br>11.3<br>21.3 |

Table 1-continued

Shoot treatment test/powdery mildew of cereal/protective

| Active compound | | Active compound concentration in the spray liquor in % by weight | Infection in % of the untreated control |
|---|---|---|---|
| 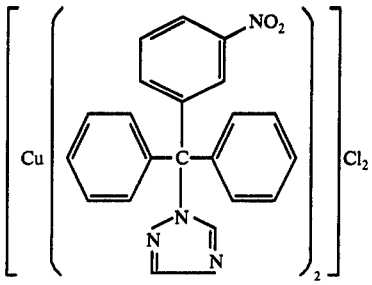 | (13) | 0.01<br>0.0025<br>0.001 | 0.0<br>16.9<br>41.3 |
| 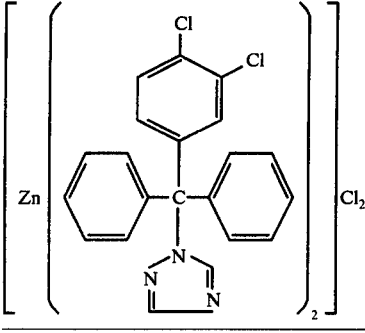 | (2) | 0.01<br>0.0025 | 7.5<br>25.0 |

EXAMPLE 2

Podosphaera test (powdery mildew of apples)/protective

Solvent: 4.7 parts by weight of acetone
Emulsifier: 0.3 part by weight of alkylarylpolyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C and at a relative atmospheric humidity of 70%. They were then inoculated by dusting with conidia of the apple powdery mildew causative organism (*Podosphaera leucotricha*) and placed in a greenhouse at a temperature of 21°–23° C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following Table:

Table 2

Podosphaera test/protective

| Active compound | | Infection in % of the infection of the untreated control at an active compound concentration (in % by weight) of | |
|---|---|---|---|
| | | 0.0008 | 0.0005 |
| 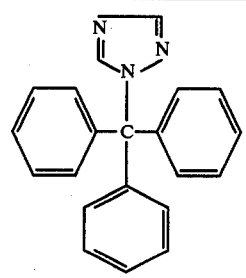 | (known)<br>(C) | 52 | — |

At an active compound concentration (in % by weight) of

Table 2-continued
Podosphaera test/protective
| | | 0.00125 | 0.00082 |
|---|---|---|---|
| (known) (A) | | 26 | 41 |
| Active compound | | Infection in % of the infection of the untreated control at an active compound concentration (in % by weight) of 0.0005 |
|---|---|---|
| | (14) | 10 |
| | (2) | 4 |
| | (16) | 1 |
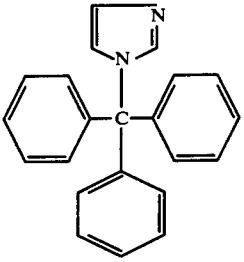

Table 2-continued
Podosphaera test/protective

| Active compound | | |
|---|---|---|
| [Cu{(3-Cl-C6H4)(C6H5)2C-N(1,2,4-triazole)}4]Cl2 | (9) | 1 |
| [Cu{(2-Cl-C6H4)(C6H5)2C-N(1,2,4-triazole)}2]Cl2 | (10) | 10 |
| [Cu{(3-I-C6H4)(C6H5)2C-N(1,2,4-triazole)}2]Cl2 | (11) | 4 |

| Active compound | | Infection in % of the infection of the untreated control at an active compound concentration (in % by weight) of | |
|---|---|---|---|
| | | 0.00125 | 0.00062 |
| [Cu{(2-Cl-C6H4)(C6H5)2C-N(imidazole)}]Cl2 | (3) | 1 | 4 |

Table 2-continued

Podosphaera test/protective

| Compound | | |
|---|---|---|
| [Cu(C(3-ClC₆H₄)(C₆H₅)₂(imidazole))₄]Cl₂ (4) | 0 | 1 |
| [Cu(C(3-ClC₆H₄)(C₆H₅)₂(imidazole))₂]Cl₂ (1) | 1 | — |

EXAMPLE 3

Erysiphe test

Solvent: 4.7 parts by weight of acetone
Emulsifier: 0.3 part by weight of alkylarylpolyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23°–24° C and at a relative atmospheric humidity of about 75%.

After 12 days, the infection of the cucumber plants was determined as a percentage of the untreated but also inoculated control plants. 0% means no infection; 100% means that the infection was exactly as great as in the case of the control plants.

The active compounds, the concentrations of the active compounds and the results can be seen from the following Tables 3a and 3b.

Table 3a

Erysiphe test

| Active compound | Infection in % of the infection of the untreated control at an active compound concentration (in % by weight) of | |
|---|---|---|
| | 0.0002 | 0.00025 |
| triphenylmethyl-1,2,4-triazole (known) (C) | 83 | — |

Table 3a-continued
Erysiphe test
| Active compound | | Infection in % of the infection of the untreated control at an active compound concentration (in % by weight) of | |
|---|---|---|---|
| | | 0.0002 | 0.00025 |
| 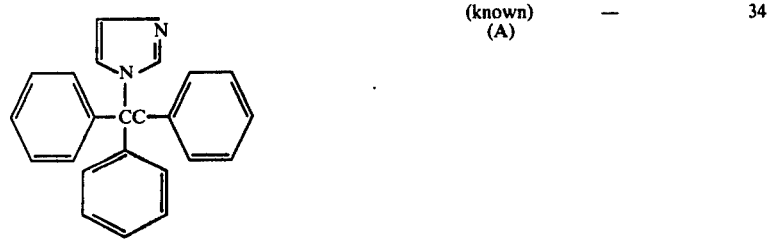 | (known) (A) | — | 34 |
| 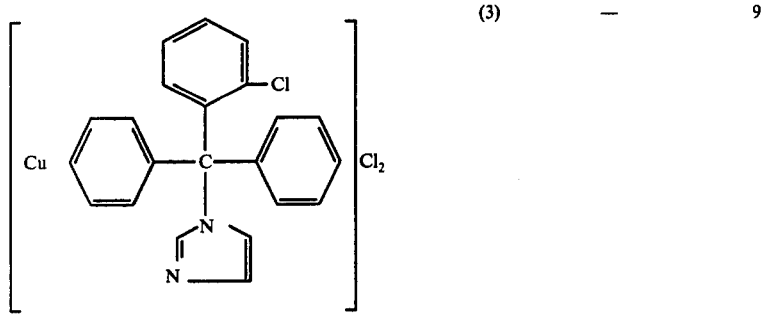 | (3) | — | 9 |
| 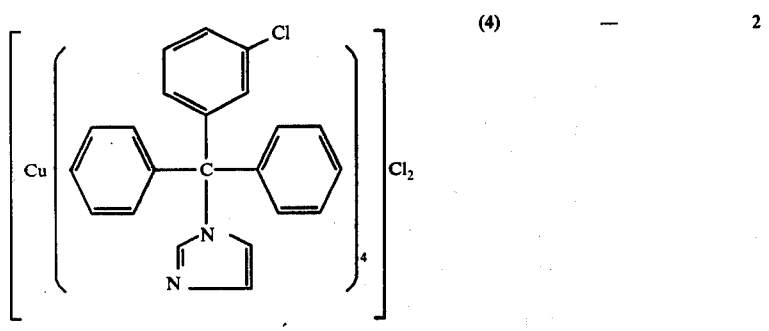 | (4) | — | 2 |
| 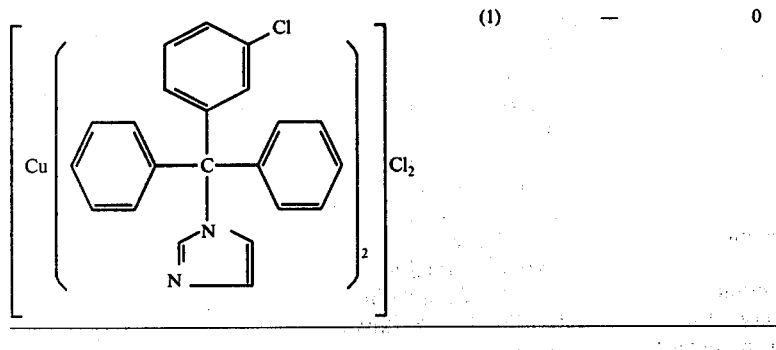 | (1) | — | 0 |

Table 3b

| Active compound | | Infection in % of the infection of the untreated control at an active compound concentration (in % by weight) of 0.0001 |
|---|---|---|
| [Cu{C(C₆H₅)₂(3-CF₃-C₆H₄)(1,2,4-triazol-1-yl)}₂]Cl₂ | (5) | 2 |
| [Zn{C(C₆H₅)₂(3,4-Cl₂-C₆H₃)(1,2,4-triazol-1-yl)}₂]Cl₂ | (2) | 19 |
| [Zn{C(C₆H₅)₂(3-Cl-C₆H₄)(1,2,4-triazol-1-yl)}₂]Cl₂ | (16) | 1 |

EXAMPLE 4

Mycelium growth test
Nutrient medium used:
20 parts by weight of agar-agar
200 parts by weight of potato decoction
5 parts of weight of malt
15 parts by weight of dextrose
5 parts by weight of peptone
2 parts by weight of disodium hydrogen phosphate
0.3 part by weight of calcium nitrate
Composition of the solvent mixture
0.19 part by weight of DMF or acetone
0.01 part by weight of emulsifier (alkylaryl polyglycol ether)

<u>1.80 parts by weight of water</u>
2 parts by weight of solvent mixture

Ratio of solvent mixture of nutrient medium:
2 parts by weight of solvent mixture
100 parts by weight of agar nutrient medium
The amount of active compound required for the desired active compound concentration in the nutrient medium was mixed with the stated amount of solvent mixture. The concentrate was thoroughly mixed in the nutrient medium mentioned and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:
1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 4
Mycelium growth test
| Active compound | Active compound concentration ppm 10 | Fungi | | | | | |
|---|---|---|---|---|---|---|---|
| | | Colletotrichum coffeanum | Cochliobulus miyabeonus | Verticillium alboatrum | Pyricularia oryzae | Phialophora cinerescens | Mycosphaerella musicola |
| 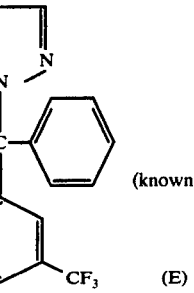 (known) (E) | | 9 | 9 | 9 | 5 | 9 | 5 |
| 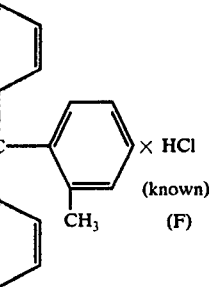 (known) (F) | | 9 | 9 | 9 | 9 | 9 | 7 |
| 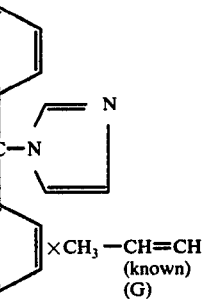 (known) (G) | | 9 | 9 | 9 | 7 | 9 | 9 |
| 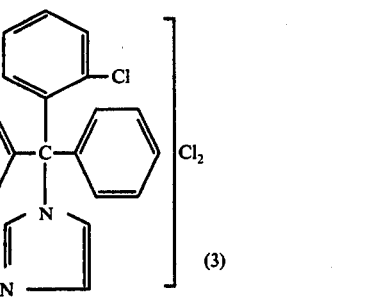 (3) | | — | 5 | 3 | 1 | 1 | 1 |
| 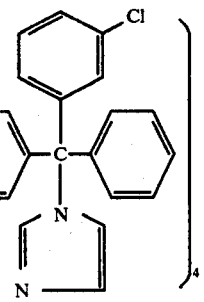 (4) | | — | 1 | 5 | 1 | 1 | 1 |

Table 4-continued

Mycelium growth test

| Active compound | Active compound concentration ppm 10 | Colleto-trichum cof-feanum | Cochlio-bulus miya-beonus | Verti-cillium albo-atrum | Pyri-cularia oryzae | Phialo-phora ciner-escens | Mycos-phaerella musicola |
|---|---|---|---|---|---|---|---|
| 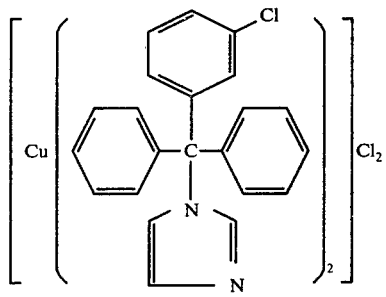 (1) | | 5 | 1 | 5 | 1 | 1 | 1 |
| 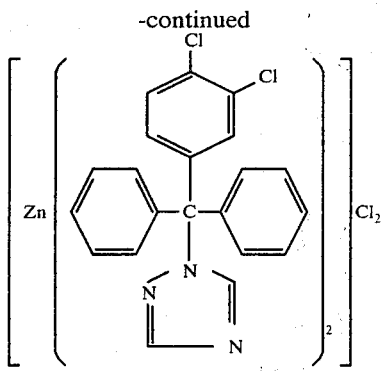 (5) | | 5 | 1 | 5 | 1 | 3 | 1 |

The following further examples are set forth to illustrate, without limitation, the manner of producing the instant compounds according to the present invention.

EXAMPLE 5

(1)

4.25 g (0.025 mole) of copper dichloride (CuCl$_2$ × 2H$_2$O) were dissolved in 10 ml of water and the solution was added dropwise, while stirring, to 17 g (0.05 mole) of 1-(m-chlorophenyl-diphenyl-methyl)-imidazole, dissolved in 100 ml of ethanol. After stirring for one hour at room temperature, the solid was filtered off, washed with diethyl ether and recrystallized from 150 ml of ethanol. This gave 13 g of dark blue crystals (64.3% of theory) of bis[1-(m-chloro-phenyldiphenyl-methyl)-imidazole]-copper-(II) chloride of melting point 113° - 115° C (with decomposition).

EXAMPLE 6

(2)

3.4 g (0.025 mole) of ZnCl$_2$ were dissolved in 15 ml of ethanol and the solution was added dropwise, while stirring, to 19.4 g (0.05 mole) of 1-(3,4-dichlorophenyl-diphenyl-methyl)-1,2,4-triazole, dissolved in 400 ml of ethanol. After stirring for one hour at room temperature, the precipitate formed was filtered off and rinsed with a little ethanol. 21 g of colorless solid (93.8% of theory) of bis-[1-(3,4-dichlorophenyl-diphenyl-methyl)-1,2,4-triazole]-zinc-(II) chloride of melting point 136° to 138° C were obtained.

The following compounds of the general formula

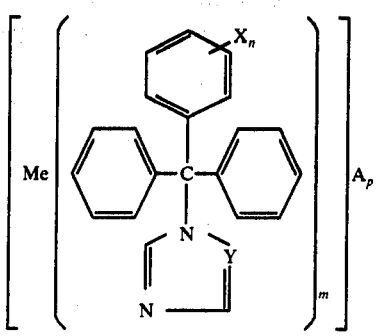

in which
Me, X, Y, A, m, n and p have the meanings indicated, were prepared analogously:

Table 5

| Compound No. | Me | X | n | Y | m | A | p | Melting point (° C) |
|---|---|---|---|---|---|---|---|---|
| 3 | Cu | 2-Cl | 1 | CH | 1 | Cl | 2 | 230 |
| 4 | Cu | 3-Cl | 1 | CH | 4 | Cl | 2 | 216.217 |
| 5 | Cu | 3-$CF_3$ | 1 | N | 2 | Cl | 2 | 157 (decomposition) |
| 6 | Cu | 2-F | 1 | N | 2 | Cl | 2 | 203–206 |
| 7 | Cu | 3,4-Cl | 2 | N | 2 | Cl | 2 | 172–176 |
| 8 | Cu | 4-Cl | 1 | N | 2 | Cl | 2 | 175–174 |
| 9 | Cu | 3-Cl | 1 | N | 4 | Cl | 2 | 161 |
| 10 | Cu | 2-Cl | 1 | N | 2 | Cl | 2 | 228–233 |
| 11 | Cu | 3-I | 1 | N | 2 | Cl | 2 | 195–197 |
| 12 | Cu | 2-$CH_3$ | 1 | N | 2 | Cl | 2 | 208–210 |
| 13 | Cu | 3-$NO_2$ | 1 | N | 2 | Cl | 2 | 212–215 |
| 14 | Cu | 3-$CH_3$ | 1 | N | 2 | Cl | 2 | 89–91 |
| 15 | Cu | — | 0 | N | 2 | Cl | 2 | 209–214 |
| 16 | Zn | 3-Cl | 1 | N | 2 | Cl | 2 | 93–95 |
| 17 | Zn | 4-Cl | 1 | N | 2 | Cl | 2 | 151 |

Other compounds which can be similarly prepared include:

Table 6

| Me | X | n | Y | m | A | p |
|---|---|---|---|---|---|---|
| Mn | 4-Br | 1 | CH | 2 | Br | 6 |
| Sn | 4-CN | 1 | CH | 2 | I | 4 |
| Mg | 3-OH | 1 | CH | 2 | Cl | 2 |
| Ni | 3-$OC_3H_7$i | 1 | CH | 2 | $NO_3$ | 2 |
| Cu | 4-S—$C_2H_5$ | 1 | N | 2 | Cl | 2 |
| Fe | 3-$COOC_3H_7$i | 1 | N | 2 | $SO_4$ | 1 |
| Fe | 4-2,2,2-trichloro-ethyl | 1 | N | 2 | $PO_4$ | 1 |
| Zn | 3-$SO_2C_4H_9$ | 1 | N | 2 | Cl | 2 |
| Cu | 2,4,5-triCl | 3 | N | 2 | Cl | 1 |
| Cu | 3-Cl-5-$C_3H_7$ | 2 | CH | 2 | Cl | 2 |

What is claimed is:
1. A metal complex of an N-tritylazole of the formula

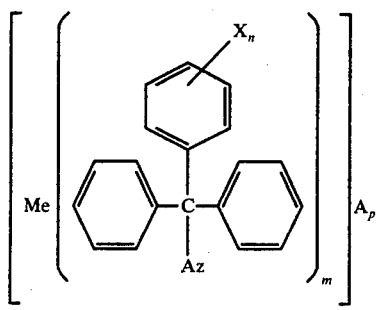

in which
Me is copper or zinc

X is halogen, nitro, cyano, hydroxyl, alkyl with up to 6 carbon atoms, akloxy with 1 or 2 carbon atoms, alkylthio with 1 or 2 carbon atoms, alkoxycarbonyl with a total of up to 5 carbon atoms, haloalkyl with 1 or 2 carbon atoms and up to 5 fluorine or chlorine atoms, or alkylsulfonyl with 1 or 2 carbon atoms, Az is an imidazolyl radical or a 1,2,4-triazolyl radical, A is a chloride, bromide, iodide, nitrate, sulfate or phosphate anion, n is 0, 1, 2, 3 or 4, m is 1, 2, 3 or 4, and p is 1, 2, 3, 4, 5 or 6.

2. A compound according to claim 1 in which n is 0, 1, 2 or 3, and p is 1, 2, 3 or 4.

3. A metal complex according to claim 1, wherein such complex is bis-[1-(m-chloro-phenyl-diphenyl-methyl)-imidazole]-copper-(II) chloride of the formula

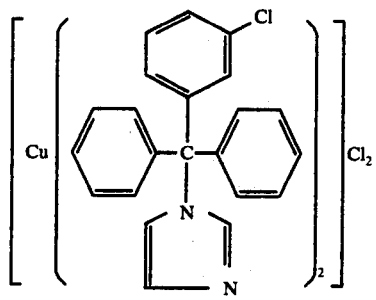

4. A metal complex according to claim 1, wherein such complex is bis-[1-(3,4-dichlorophenyl-diphenyl-methyl)-1,2,4-triazole]-zinc-(II) chloride of the formula

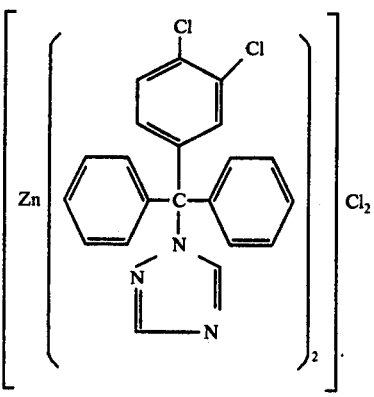

5. A metal complex according to claim 1, wherein such complex is bis-[1-(o-chloro-phenyl-diphenyl-methyl)-imidazole]-copper-(II) chloride of the formula

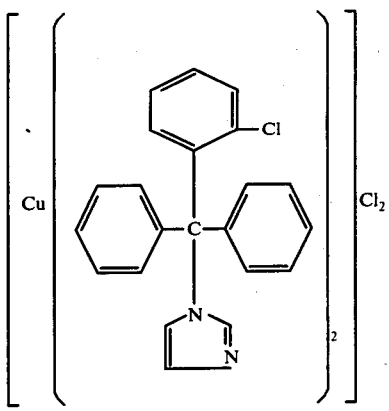

6. A metal complex according to claim 1, wherein such complex is tetra-[1-(m-chloro-phenyl-diphenyl-methyl)-imidazole]-copper-(II) chloride of the formula

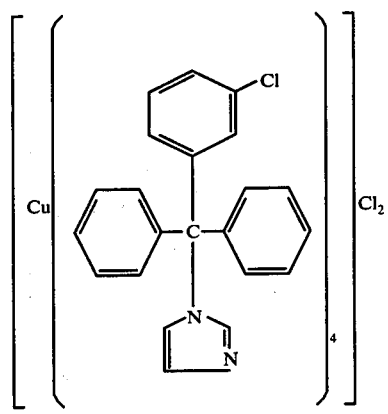

7. A metal complex according to claim 1, wherein such complex is bis-[1-(m-trifluoromethyl-phenyl-diphenyl-methyl)-1,2,4-triazole]-copper-(II) chloride of the formula

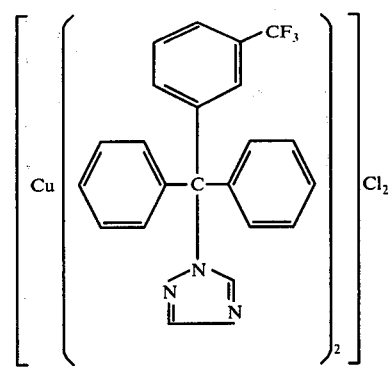

8. A fungicidal composition containing as active ingredient a fungicidally effective amount of a complex according to claim 1 in admixture with a diluent.

9. A method of combatting fungus pests which comprises applying to the pests or a habitat thereof a fungicidally effective amount of a complex according to claim 1.

10. The method according to claim 9 in which said complex is
bis-[1-(m-chloro-phenyl-diphenyl-methyl)-imidazole]-copper-(II) chloride,
bis-[1-(3,4-dichlorophenyl-diphenyl-methyl)-1,2,4-triazole]-zinc-(II) chloride,
bis-[1-o-chloro-phenyl-diphenyl-methyl)-imidazole]-copper-(II) chloride,
tetra-[1-(m-chloro-phenyl-diphenyl-methyl)-imidazole]-copper-(II) chloride or
bis-[1-(m-trifluoromethyl-phenyl-diphenyl-methyl)-1,2,4-triazole]-copper-(II) chloride.

* * * * *